United States Patent

Suga

[11] Patent Number: 5,302,128
[45] Date of Patent: Apr. 12, 1994

[54] DENTAL IMPLANT

[76] Inventor: Shinichi Suga, 25-9, Fukasawa 5-chome, Setagaya-ku, Tokyo, Japan

[21] Appl. No.: 929,258

[22] Filed: Aug. 13, 1992

[30] Foreign Application Priority Data

Dec. 6, 1991 [JP] Japan .................................. 3-108951

[51] Int. Cl.$^5$ ............................................... A61C 8/00
[52] U.S. Cl. ..................................................... 433/176
[58] Field of Search ......................................... 433/176

[56] References Cited

U.S. PATENT DOCUMENTS 3,881,251  5/1975  Valen .................................. 433/176
4,802,847  2/1989  Komatsu ............................. 433/176

FOREIGN PATENT DOCUMENTS 2237598  2/1974  Fed. Rep. of Germany ...... 433/176
 728855  5/1980  U.S.S.R. ............................. 433/176

Primary Examiner—John J. Wilson
Attorney, Agent, or Firm—Lackenbach Siegel Marzullo Aronson

[57] ABSTRACT

In an implant constructed of a blade form body (2) to be implanted within an alveolar bone (10) and a head (3), the body is constructed in a bending form like saw teeth in its sectional area in a whole length direction. In the upper portion of the body, sharp portions of the saw teeth which is a positioning range of the implant in the compact bone portion (10a) of the alveolar bone (10) at the time of the implantation, are projected in a taper form so as to gradually increase the height upward.

4 Claims, 3 Drawing Sheets

DENTAL IMPLANT

BACKGROUND OF THE INVENTION

This invention relates to a dental implant.

It is publicly known that an implant acts as an artificial dental root for a denture by implanting it in the alveolar bone in order to repair a damaged tooth by implanting a denture.

Heretofore, various kinds of implants have been proposed and this invention has been anteceded by a blade-type implant.

The blade-type implant is constructed by a blade-like body and a pillar head projected towards the upper end of the body. In this case, an action which supports the denture exposes the head of the body at the time when the body is implanted in the alveolar bone.

In implanting the implant, a groove which fits the size of the implant is dug out in the alveolar bone. Then, by inserting the implant therein, an initial fixation due to friction combination is obtained, and then bone tissue in the alveolar bone increases over time and the slit between the implant and the groove is buried and connected by new raw bone. In other words, a bone setting is performed.

Thus, in the implant of the blade type, the connection of the bone by new raw bone is delayed.

However, the above conventional implant has the following problems:

(1) It is necessary to provide a groove which exactly fits the implant into the alveolar bone in order to obtain a secure initial fixation, and this operation is very difficult because it is performed in the patient's mouth. For instance, if the groove is larger than the implant, the implant wobbles, making the initial fixation inferior, and if the groove is smaller, the insertion of the implant is impossible.

(2) As a result, a secure initial fixation of the implant is impossible. In order to repair the denture, it is necessary to wait until the implant is connected to the alveolar bone through the lapse of time. Accordingly, two separate operations are required.

(3) In case (1), even if the implant fits the groove and does not wobble, its connection depends on the friction holding the implant in the groove. Accordingly, the implant buried by ultrasonic wave movement due to a high frequency vibration from a turbine could float up to the surface whereby cutting by a turbine cannot be performed near an area where the implant operation is practiced.

(4) In case (1), although the friction force becomes stronger against the implant if the groove is smaller somewhat, there exists the peril that the alveolar bone, which is forcibly widened by the implant at the time of insertion, will split.

(5) In case (1), if the contact area between the implant and the groove increases, the friction force becomes stronger. However, in this case the implant cannot enlarge its size in a total length direction in relation to the adjacent teeth, but only enlarges in the upper and lower directions. As a result, it is necessary that the groove of the alveolar bone be dug close to the jaw hole and the lower alveolar canal, and a greater risk accompanies such an operation.

(6) Since a leg at the lower end of the implant gets into the alveolar bone, particularly into spongy bone having a soft tissue, when the implant is inserted into the groove by striking the implant with a mallet at the time of implantation, the implant can sink in more than necessary. In addition, the implant can be sunk down by bite pressure even after completion of the operation.

As described above, many difficult problems are related to adopting the implant to a clinic, and the use of the implant is therefore low in Japan.

However, on the contrary, it is very useful in repairing damage to a cheek tooth or a long span bridge. In addition, there are a great many potential demands from patients who have strong aversions against dentures, and an improvement in dental implants is desired from the dental profession.

BRIEF DESCRIPTION OF THE INVENTION

This invention aims to provide an improved implant which solves the problems found in the conventional art as described above, and is characterized in that the body is constructed to bend like the teeth of a saw in a section thereof in a whole direction and with sharp portions of the saw teeth positioned within a range of a compact bone portion of the alveolar bone at the upper portion of the body which are projected at the time of the implantation so as to gradually increase its height like a taper-form according to the body's advancement in an upper direction.

DETAILED DESCRIPTION OF THE INVENTION

FIG. 1 through FIG. 4 represent one example of an implant of this invention.

Figure 1:
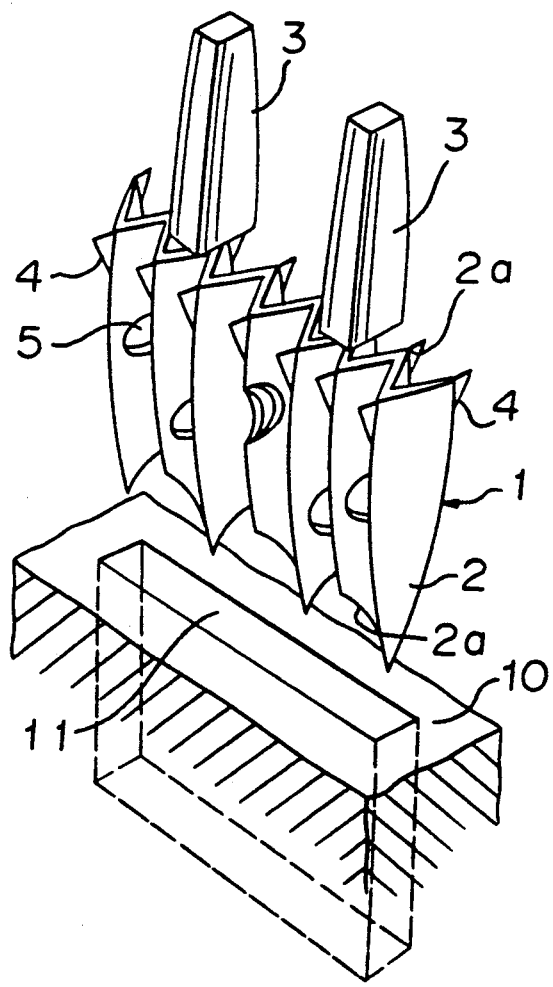
FIG. 1 is a perspective view of an implant of this invention.

The numeral 1 in FIG. 1 is an implant of this invention, said implant 1 being constructed of a body inserted into a groove 11 dug into the alveolar bone 10 and a head 3 for supporting the denture (not shown particularly).

Further, in this example, since bone setting after implantation is excellent, a pure titanium implant which is biocompatible is adopted as the implant element.

The above body 2 is constructed in a bending form like saw teeth along the whole length direction thereof. In this invention, the body 2 is constructed to be a wedge which converges the width of the saw teeth toward the lower portion (see FIG. 4).

Furthermore, in this invention, the top end of the leg 2b at the lower end of the body 2 is formed very sharp.

The numeral 2 in FIG. 5 is a vent of round window form bored in the body 2 which performs the conventionally known operation which fixes the implant 1 by being buried in the new bone formed after a lapse of time after implantation in the alveolar bone.

The numeral 4 in the Figures is a projection provided at the upper portion of the body 2, said projection being formed to be a taper wherein the height of the sharp portion of the saw teeth gradually increases from halfway of the upper portion of the body to a neck shoulder 2a at the top end of the body, with an especially sharp ridge line being formed thereon.

Figure 4:
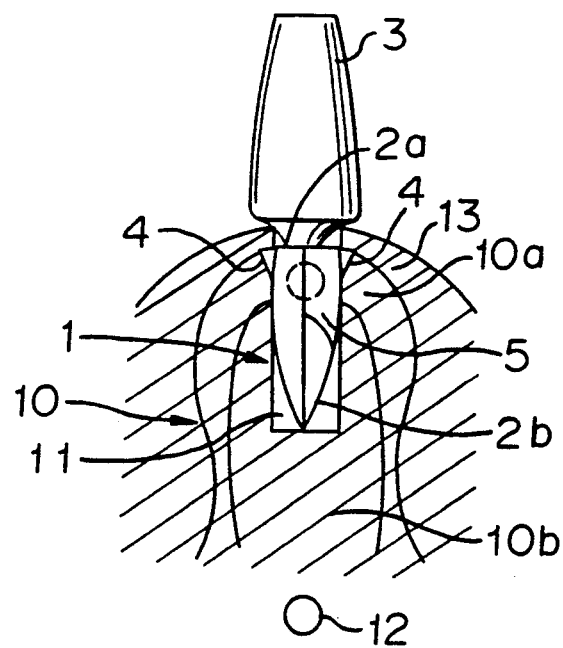
FIG. 4 is a sectional view taken along line 4—4 in FIG. 2.

This projection 4 is provided within a range which is positioned at a layer portion of the compact bone 10a (generally about 4 to 5 mm in thickness) of the alveolar bone 10 at the time of implantation of the implant (see FIG. 4).

In the example, the height of the body 2 and the height of the projection are estimated to be approximately 8 mm and 2 mm, respectively.

Figure 2:
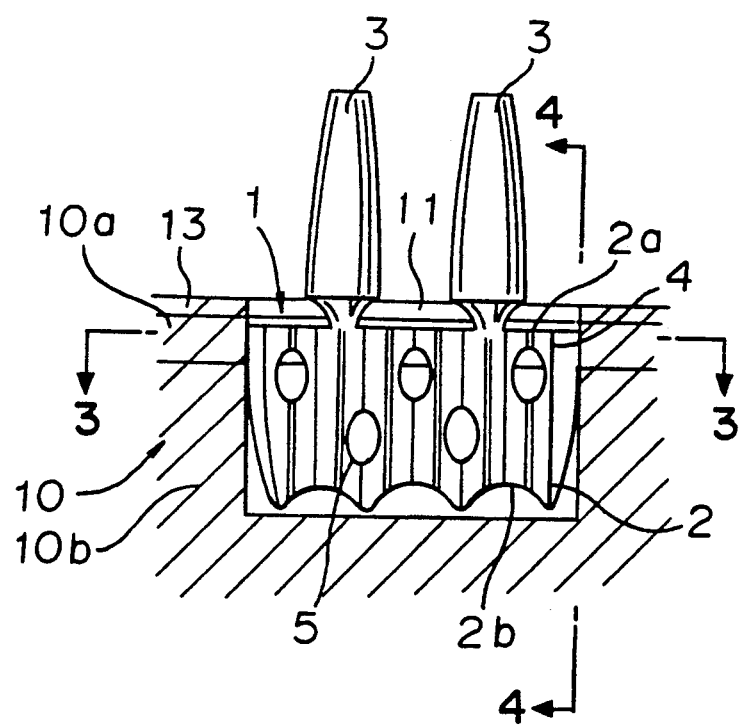
FIG. 2 is an elevation view at the time of the implantation bone of the implant of this invention.
Figure 3:
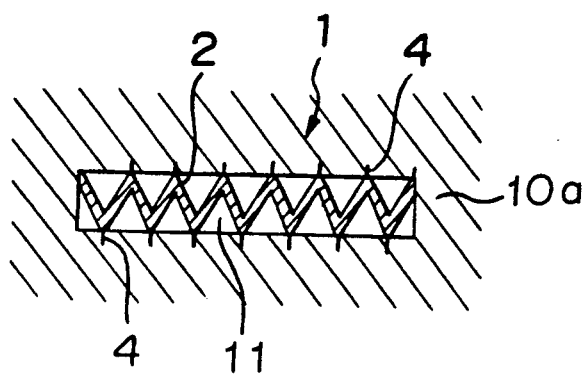
FIG. 3 is a sectional view taken along line 3—3 of FIG. 2

From the above construction, the implant of this invention is provided for use by being inserted into the groove 11 bored in the alveolar bone 10 (see FIG. 2 to FIG. 4).

The numeral 10b in the Figures is a spongy bone, 13 is a gingiva and 12 is a lower alveolar canal. Accordingly, according to the implant of this invention, since the body 2 is constructed in a saw teeth form in the long direction, a flexible operation in a squashed direction of the saw teeth can be expected even if it is constructed of a hard metallic element and the body is flexible in a squashed direction of the saw teeth even if the width of the body against the groove 11 is larger, whereby a smooth insertion of the body in the groove is achieved without providing an excess load in the width direction to the alveolar bone 10. Accordingly, since the squashed saw teeth after insertion returns the groove to the original direction, a strong frictional connection is achieved between the implant and the groove.

Further, when the saw teeth of the body 2 are constructed in a wedge and side form which converges the width of the saw teeth towards the lower end thereof as shown in the example and the top end of the leg 2b at the lower end thereof is formed sharply, the above insertion becomes easier.

Secondly, since the taper-form projection 4 which gradually increases the height of the portion of the saw teeth to a neck shoulder 2a at the upper end of the body 2 is provided, the projection gradually encroaches into an inner wall of the groove 11 by striking the implant with a mallet at the time of the insertion in the grove 11, whereby a smooth insertion of the body into the groove is possible.

Furthermore, by this encroaching, the movement of the implant after insertion is prevented entirely together with the above first operation.

In this case, when the ridge line portions of the overhang portion 4 in the example are formed sharply, the encroaching is performed more securely.

Since this projection 4 is provided with a range which is positioned at a layer portion of the compact bone 10a in the alveolar bone 10 at the time of implantation of the implant, the body 2 is not supported by a soft spongy bone 10b, but by a strong compact bone different from the conventional implant whereby unnecessary sinking of the implant due to bite pressure at the time of striking with a mallet and after completion of the implant operation is prevented.

Thirdly, the cracking of the alveolar bone in a width direction can be prevented by the following three operations even if the body is struck with a mallet in the insertion direction at the time of insertion.

(1) The ridge line portion of the saw teeth contacts with the inner wall of the groove 11 uniformly at the time of insertion by making the body 2 in a saw teeth form, and as a result the load in the width direction of the alveolar bone 10 caused by insertion of the body is dispersed uniformly.

(2) The ridge portion of the saw teeth abuts against the inner wall of the groove 11 of the alveolar bone 10 in a wedge form whereby a part of a load in the width direction of the alveolar bone at the time of the insertion is dispersed in the longitudinal direction.

(3) As a result of the ridge line of the projection 4 being formed in a taper which gradually increases the height toward the upper direction, the body encroaches into the alveolar bone whereby a part of the load in the width direction of the alveolar bone 10 is absorbed.

Further, it is needless to say that in case that the ridge line portion of the projection as shown in the example is formed sharply, the operation of the above (3) is displayed more strongly.

Fourthly, since the body 2 is constructed in saw-teeth form, a very large surface area can be secured compared with the whole length and height of the body. As a result, when the bone tissue within the alveolar bone increases as time passes after the implantation, the area to be subjected to bone setting increases considerably and causes a strong combination between the implant and the alveolar bone.

The invention constructed as above has the following effects.

(1) Since the implant is strongly inserted into the alveolar bone by a pushing force against the groove of the alveolar bone of the saw teeth like body portion and the encroaching of the projection to the compact bone, a very strong initial fixing can be obtained.

(2) As a result of the effect of (1), the repair of the denture can be obtained immediately without awaiting the bone setting between the implant and the alveolar bone as in the conventional art. Accordingly, the operation is completed all at one time.

(3) As a result of the effect of (1), the floating of the implant due to the ultrasonic movement can be prevented even in use of a turbine for dentistry.

(4) Since the implant is inserted into the groove smoothly by the flexibility in the squashed direction of the saw teeth against the groove of the saw teeth form of the body portion, the carving of the groove requiring high accuracy is alleviated, and the implant operation can be performed with ease and without error.

(5) Since the body is supported with a strong compact bone by the projection, unnecessary sinkage of the implant due to bite pressure when striking with a mallet after prosthesis, is prevented.

(6) Since a very large surface area can be secured compared with the whole length and the height of the body by the saw teeth-like body portion, when the bone tissue within the alveolar bone increases over time after implantation, the area to be subjected to the bone setting increases so much and a strong combination is created between the implant and the alveolar bone. By this, strong fixation without movement or sinking is obtained together with the effect of the above (1).

(7) As a result of the effect of (6), since there is no need to increase the height of the body for securing the surface area, there is no need to dig the groove of the alveolar bone to the vicinity of the jaw hole and the lower alveolar canal. The risk of the operation therefore decreases.

(8) Since the body is in saw teeth form, the ridge line portion abuts against the groove of the alveolar bone like a wedge type and a part of the load in the width direction of the alveolar bone applied at the time of the insertion is dispersed in the longitudinal direction thereof. By this, the striking of the implant with a mallet or the like which could not be used for fear of cracking in the width direction of the alveolar bone becomes safely possible while the load in the width direction is dispersed uniformly and projection can be encroached.

What I claim is:

1. A dental implant for insertion in an elongated rectangular groove formed with side walls in the alveolar bone of a body, comprising a body of saw tooth form in cross section with a plurality of tapering teeth with a top zigzag surface adapted for implantation in said alveolar bone of said body, and at least one integral head extending upwardly therefrom for supporting a denture; said dental implant having small, thin sharp triangular pointed projections extending outwardly from a crest on each saw tooth adjacent said top zigzag surface so as to contact said side walls of the groove formed in the alveolar bone at the time of insertion; whereby an immediate strong friction connection is obtained between said groove and said implant in one step or operation, and cracking of said alveolar bone is minimized due to the compression of said dental implant body in the elongated direction of said groove and by the dispersion of the load in a transverse direction of the groove by said small, thin, sharp, triangular-pointed projections which wedge in place near the top surface of said alveolar bone.

2. A dental implant according to claim 1 wherein a ridge line of a projection (4) is formed sharply.

3. A dental implant according to claim 1 or claim 2 wherein a side form of the saw teeth of body (2) is formed to be a wedge form which converges its width towards to the lower end of the body.

4. An implant for dentistry according to either one of claim 1 or claim 3 wherein said lower end of the body (2) is formed sharply.

* * * * *